United States Patent [19]

Way et al.

[11] Patent Number: 5,080,099
[45] Date of Patent: * Jan. 14, 1992

[54] MULTI-PAD, MULTI-FUNCTION ELECTRODE

[75] Inventors: Tim J. Way, Carlsbad; L. Allan Butler, Oceanside, both of Calif.

[73] Assignee: Cardiotronics, Inc., Carlsbad, Calif.

[*] Notice: The portion of the term of this patent subsequent to Sep. 11, 2007 has been disclaimed.

[21] Appl. No.: 575,133

[22] Filed: Aug. 29, 1990

Related U.S. Application Data

[63] Continuation of Ser. No. 237,513, Aug. 26, 1988, Pat. No. 4,955,381.

[51] Int. Cl.$^5$ .................... A61B 5/0402; A61N 1/04
[52] U.S. Cl. .................... 128/640; 128/798; 128/419 D
[58] Field of Search .................... 128/639–641, 128/644, 783, 798, 799, 802, 803, 419 D

[56] References Cited

U.S. PATENT DOCUMENTS

| | | | |
|---|---|---|---|
| 3,547,108 | 12/1970 | Seiffert | 128/712 |
| 3,612,061 | 10/1971 | Collins et al. | 128/799 |
| 3,721,246 | 3/1973 | Landis | 128/783 |
| 3,848,600 | 11/1974 | Patrick, Jr. et al. | 606/32 |
| 3,862,636 | 1/1975 | Bell et al. | 128/419 D |
| 3,865,101 | 2/1975 | Saper et al. | 128/696 |
| 3,886,950 | 6/1975 | Ukkestad et al. | 128/419 D |
| 3,960,141 | 6/1976 | Bolduc | 128/639 |
| 3,961,623 | 6/1976 | Milani et al. | 128/639 |
| 3,977,392 | 8/1976 | Manley | 128/641 |
| 4,094,310 | 6/1978 | McEachern et al. | 128/712 |
| 4,177,817 | 12/1979 | Bevilacqua | 128/802 |
| 4,265,253 | 5/1981 | Abraham | 128/798 |
| 4,291,707 | 9/1981 | Heilman et al. | 128/419 D X |
| 4,349,030 | 9/1982 | Belgard et al. | 128/419 PG |
| 4,355,642 | 10/1982 | Alferness | 128/419 D X |
| 4,365,634 | 12/1982 | Bare et al. | 128/798 X |
| 4,419,998 | 4/1985 | Heath | 128/639 |
| 4,494,552 | 1/1986 | Heath | 128/696 |
| 4,619,266 | 10/1986 | Hodgson | 128/798 X |
| 4,763,660 | 8/1988 | Kroll et al. | 128/640 |
| 4,955,381 | 9/1990 | Way et al. | 128/640 |

FOREIGN PATENT DOCUMENTS 0193480  9/1986  European Pat. Off. .............. 128/78

OTHER PUBLICATIONS

Ketecho, Inc. Advertising Brochure for K-STIK (per attached defibrillator pads).
3n Advertising Brochure for Littman Defib-Pads.
Andover Medical Advertising Brochure for Paddle Pads.
Medtronic Advertising Brochure for Compact Ease and Neuro Aid Families of Tens and Nines Electrodes.
Promeon Advertising Brochure for Hydrogels.
R. Kaner and A. MacDiavmid, "Plastics that Conduct Electricity", Scientific American, vol. 258, No. 2, (2,1988).

Primary Examiner—Lee S. Cohen
Attorney, Agent, or Firm—Lyon & Lyon

[57] ABSTRACT

An electrode having multiple conductive polymer pads for performing multiple, electrical physiological functions from a single set of electrodes with respect to a patient at or about the same time, such as defibrillating, pacing, and monitoring of that patient's heart, is described. The electrode is advantageously integrated into a cardiac system having stimulating means coupled to the electrode for delivering electrical impulses to the electrode to be used to stimulate the patient's heart, and monitoring means also coupled to the electrode for receiving and displaying electrical impulses produced by the patient's heart. The conductive polymers which comprise the pads are optionally inherently adhesive, so that the pads will adhere to a patient's body over their entire surface area. Moreover, they are rubber-based, will not smear or leave a residue on a patient's skin, have lower impedance, and depolarize faster compared with present saline-based gels, further contributing to the multi-functional capability. Also, the other impedance enables the voltage generator in the cardiac system of which the electrode is part to deliver a particular current pulse with less voltage, enabling the voltage generator, and the cardiac system in general, to be smaller, more compact, and less costly.

12 Claims, 1 Drawing Sheet

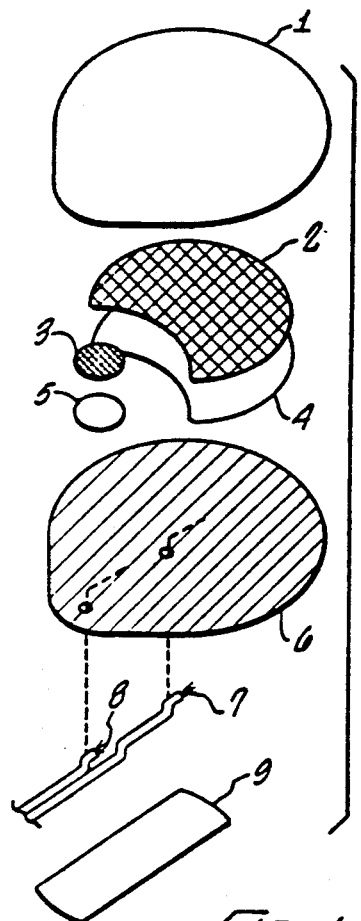
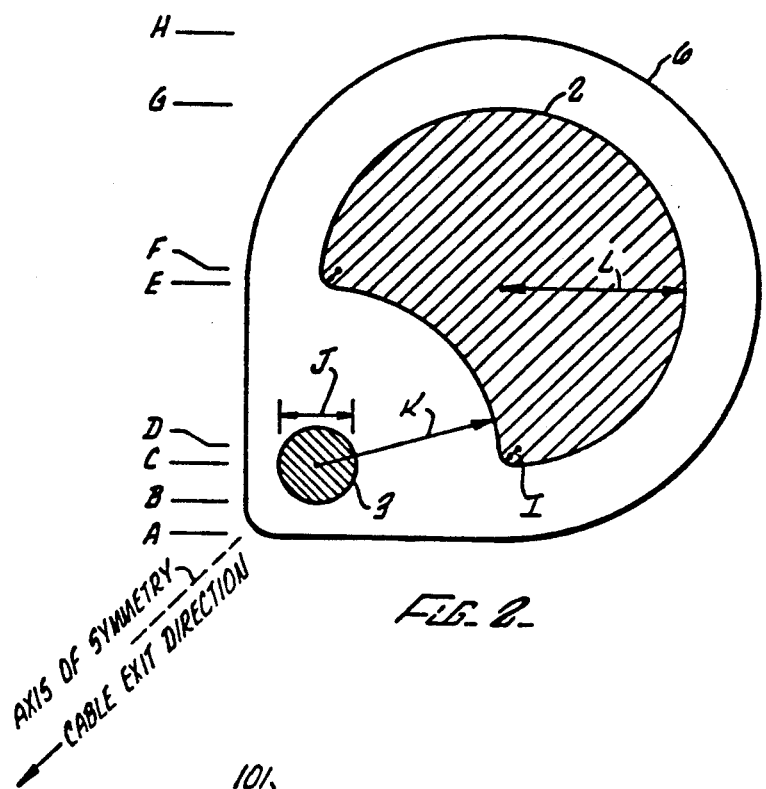
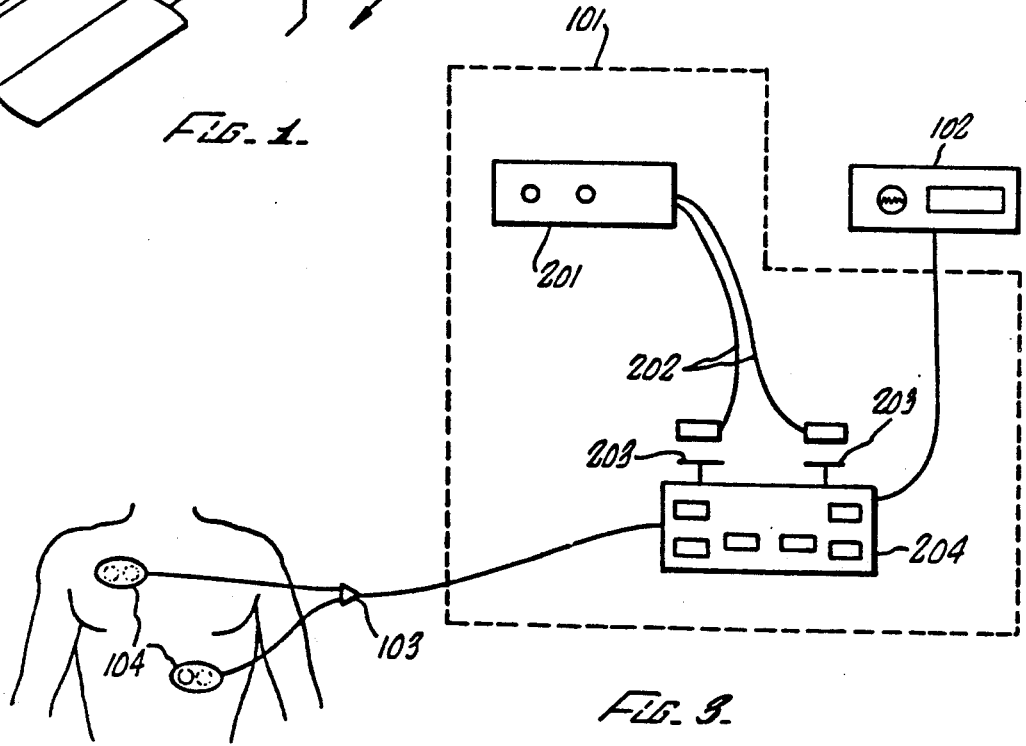

MULTI-PAD, MULTI-FUNCTION ELECTRODE

This application is a continuation application of U.S. patent application Ser. No. 237,513, filed Aug. 26, 1988, now U.S. Pat. No. 4,955,381.

BACKGROUND OF THE INVENTION

1. Field of the Invention

This invention relates generally to a multi-pad, multi-function electrode, and more specifically, to an electrode having multiple conductive polymer pads which enable a single set of electrodes to perform multiple electrical, physiological functions with respect to a patient, such as monitoring and stimulating of the patient's heart, at or about the same time.

2. Background Information

Prior art electrodes have traditionally been single-function electrodes which can be divided into two classes according to their function, whether monitoring or stimulation. A monitoring electrode is used to transfer electrical impulses from a patient's body to a cardiac system which usually displays the impulses to permit monitoring of that patient's heart condition; a stimulating electrode, on the other hand, is used to deliver stimulating electrical impulses from a cardiac system to a patient's body to permit either defibrillation or external pacing of that patient's heart.

The prior art monitoring and stimulating electrodes differ quite a bit in their physical characteristics. The monitoring electrode, for example, is typically 2-4 cm. in diameter with a single 1-2 cm. conductive center pad for receiving electrical impulses from a patient's heart, and delivering them to a monitor. The stimulating electrode, on the other hand, at least a stimulating electrode for delivering high energy to a patient for either defibrillation or external cardiac pacing, is typically 10-14 cm. in diameter with a single 8-12 cm. conductive center pad for delivering electrical impulses to a patient's heart from a voltage or current generator of a cardiac system.

The majority of prior art electrodes, whether for stimulating or monitoring, are constructed similarly. They are made of a flexible foam backing attached to a piece of metal foil with a connecting lead attached to the center. The foil in turn is attached to a conductive gel-filled sponge which is surrounded by a ring of flexible adhesive foam for attachment to a patient's skin.

These prior art electrodes suffer from a number of problems. First, they are severely limited in their ability to perform multiple electrical, physiological functions with respect to a patient from a single set of electrodes. As a result, it is necessary to either perform multiple electrical, physiological functions sequentially from a single set of electrodes, or else use multiple sets of electrodes simultaneously, in order to deliver multiple electrical, physiological functions to a patient. Each one of these approaches has an associated set of problems.

Sequential defibrillating and monitoring from a single set of prior art electrodes, although possible, will in many cases necessitate a long wait between the performance of the monitoring and defibrillating functions until the electrodes have depolarized, i.e. discharge stored energy (see ensuing discussion). This will in many instances result in delays in delivering necessary care to a patient under emergency conditions, which can have disastrous consequences.

Also, sequential pacing and monitoring from a single set of electrodes will simply be impossible since a pacing pulse must be administered at least sixty times per minute, and there will be insufficient time between the application of the pacing pulses for the electrodes to depolarize, i.e., discharge energy from the pacing pulses which has been stored in the electrodes through a process called polarization. Since there may be insufficient time for the electrodes to depolarize, i.e. discharge the stored energy, before the electrodes are used to monitor, the stored energy will mask the electrical impulses being received from the patient's heart, and accurate monitoring will be impossible.

The theoretical basis for how an electrode stores energy is that the electrode effectively forms a capacitor, with the metal foil forming one plate of the "capacitor," the internal "wet" portion of the body forming the second plate, and the conductive pad (typically a gel-filled sponge) comprising the material placed between the "capacitor" plates. When the electrode is used to stimulate a patient's heart, and a current pulse is delivered through the electrode to effectuate either pacing or defibrillation, the voltage between the "capacitor" plates builds up slowly, typically to levels of several hundred millivolts. The voltage takes time to build up as the material between the "capacitor" plates, i.e. the conductive pad, polarizes in order to store charge.

However, once the sponge-filled gel is polarized, it will take time to depolarize. Therefore, long after the current pulse has been applied, the "capacitor" will still retain a voltage of several hundred millivolts until the conductive pad depolarizes, and the "capacitor" discharges. Since effective monitoring must be sensitive enough to pick up a signal on the order of one millivolt from a patient's body, the continued storage of charge, resulting in a voltage of several hundred millivolts remaining across the "capacitor" plates, may drown out the signal from the patient's body, making stimulation and monitoring from the same electrode, difficult, if not impossible, until the electrode depolarizes.

A problem with using multiple sets of electrodes is that it is cumbersome and unwieldy since the wires from the many sets often become twisted. The twisting of the wires is problematic since it may result in delays in delivering necessary emergency care to a patient.

Another problem is that the multiple sets of electrodes will move, and it will be difficult to ensure consistent placement of the electrodes with respect to one another. Without consistent placement of the monitoring electrodes, the visual display of a patient's heart condition may be heavily biased since it is heavily dependent on the placement of the monitoring electrode with respect to the stimulating electrode.

Prior art electrodes also suffer from problems unrelated to sequential or multiple use. For example, prior art electrodes do not typically adhere properly to a patient's skin since only a small portion of the surface area of the electrode, the ring of flexible adhesive attached to the gel-filled foam, is available for adhering to the patient's skin. As a result, the electrode will typically adhere poorly, causing the defibrillating or pacing electrical impulses to pass through the skin in the few places where contact has actually been made, leading to skin burns. Also, these electrodes may tend to move, and any movement of the monitoring electrode while monitoring is being performed will interfere with and alter the electrical impulses being received from the patient's body by introducing biases known as monitoring artifacts, which will in turn lead to inaccurate diagnosis and monitoring of the patient's heart condition. Moreover, the conducting pad in the prior art electrodes is typically a saline-based, gel-filled sponge, and movement of the electrode will cause the gel to smear over the surface of a patient's chest. The smearing of the gel further limits the ability of a single set of prior art electrodes to perform multiple electrical, physiological functions, since the smearing of the conductive gel will result in an electrical interaction between the electrical impulses being delivered and received from a patient's heart in support of the stimulation and monitoring functions. Also, besides smearing, the prior art gels will leave a residue on the patient's skin, and they may take a long time to depolarize which further limits the ability of a single set of prior art electrodes to perform multiple electrical, physiological functions.

Accordingly, it is an object of the present invention to provide an electrode having multiple conductive polymer pads which enable a single set of electrodes to perform multiple electrical, physiological functions at or about the same time, such as stimulating and monitoring of a patient's heart.

SUMMARY OF THE INVENTION

To achieve the foregoing objects, and in accordance with the purpose of the invention as embodied and broadly described herein, there is provided a multi-pad, multi-function electrode wherein each pad is composed of a conductive polymer known as a hydrogel. The hydrogel is also optionally inherently adhesive to achieve superior adhesion to a patient's skin over its entire surface area, is rubber-based and hence does not smear or leave a residue on a patient's body, and depolarizes faster and has lower impedance compared with typical prior art saline-based gels.

Since each electrode has multiple polymer pads, a set of such electrodes can better perform multiple electrical, physiological functions, such as stimulation and monitoring of a patient's heart, compared with a single set of prior art electrodes. In fact, the use of multiple polymer pads makes monitoring and pacing of a patient's heart from the same set of electrodes possible for the first time.

Since the hydrogel is optionally inherently adhesive, each pad can also achieve superior adhesion to a patient's skin over its entire surface area, eliminating or minimizing the problem of burns, poor adhesion, and movement associated with prior art electrodes. Also, since the hydrogel has lower impedance compared to the prior art gels, less voltage will be required to deliver a current pulse through the electrode in order to stimulate a patient's heart, so that the voltage generator and the cardiac system of which the electrode is a part can be smaller, more compact, and less costly.

Finally, the fact that the hydrogels depolarize faster compared to the prior art gels, further contributes to the performance of multiple electrical, physiological functions.

BRIEF DESCRIPTION OF THE DRAWINGS

FIG. 1 is a drawing showing an exploded view of an electrode incorporating the teachings of the subject invention;

FIG. 2 is a drawing showing an assembled view of an electrode incorporating the teachings of the subject invention; and FIG. 3 is a block diagram of a cardiac system incorporating an electrode of the subject invention.

DESCRIPTION OF THE PREFERRED EMBODIMENT

A diagram of an electrode incorporating the teachings of the subject invention is illustrated in FIG. 1. As indicated in the Figure, the electrode advantageously comprises peelable cover 1, stimulating polymer pad 2, monitoring polymer pad 3, stimulating metal foil 4, monitoring metal foil 5, plastic foam cover 6, stimulating insulated wire 7, monitoring insulated wire 8, and wire retainer/label 9. An object of the electrode is to perform multiple electrical, physiological functions from a single set of electrodes at or about the same time through the use of multiple polymer pads. In the example illustrated in FIG. 1, one pad is provided to deliver electrical impulses to a patient's heart in order to stimulate it, while another pad is provided to receive electrical impulses from the patient's heart in order to monitor it. The invention, however, is not limited to this specific example, and is instead meant to encompass an electrode for performing any number of electrical, physiological functions at or about the same time from a single set of electrodes, including but not limited to stimulating, defibrillating, pacing, and monitoring of a patient's heart as previously described, and also electrical therapeutic stimulation of a patient's muscles. The invention is also meant to encompass an electrode having more than two conductive polymer pads.

The peelable cover is advantageously attached to the polymer pads to keep any foreign material off of the surface of the pads, and can be peeled off when the electrode is about to be applied to a patient's skin.

The stimulating and monitoring polymer pads are preferably physically separated from one another in the layout of the surface of the electrode, as indicted in FIG. 2 (which uses the same identifying numerals as FIG. 1), in order to isolate the delivery and receipt of electrical impulses in support of the stimulating and monitoring functions.

The stimulating and monitoring pads are advantageously attached to the stimulating and monitoring metal foils, respectively, which are in turn attached to the plastic foam cover, which acts as a foam backing to both metal foils. The plastic foam cover has holes in it, exposing the stimulating and monitoring metal foils, and the stimulating and monitoring insulated wires have exposed ends which are inserted into the holes and electrically coupled to the metal foils. The plastic cover is sandwiched between the foils and the wires.

In the example of FIG. 1, the hydrogel pads are advantageously 25 mils (1 mil equals 0.001 inch) thick. Moreover, the metal foils are preferably comprised of tin since the foil will be in contact with the conductinve polymer pads, and other metals will tend to corrode when placed in contact with the pads. Also, in the example of FIG. 1, the tin foil is advantageously 3 mils thick.

The foam backing is advantageously comprised of a rubber closed-cell foam such as VOLARA. The foam is advantageously closed-cell, i.e., has air pockets completely surrounded by foam, so that no foreign material can get through it. This is to be contrasted with an open-cell material such as a sponge, which allows foreign material such as water to pass completely through it. In addition, the foam backing is advantageously covered with a medical grade adhesive which will enable the foam backing to adhere directly to the metal foils, and to the human body in those areas which are not adhered to the metal foil covers of the conductive polymer pads. In the example of FIG. 1, the foam backing is advantageously 1/16 of an inch 0.062 inches) thick, and the foam backing has two holes to allow exposure of the stimulating and monitoring metal foil coverings. As mentioned earlier, the stimulating and monitoring insulated wires have exposed ends, which are inserted into the holes and electrically coupled to the stimulating and monitoring metal foil covers, respectively.

In the example of FIG. 2, the dimensions of the electrode are provided in centimeters (cm.). As indicated in the Figure, the face of the electrode has an irregular shape and advantageously has a height of 14 cm. Moreover, the stimulating pad is also irregularly shaped and advantageously has the dimensions indicated in the Figure. In addition, the monitoring pad is advantageously shaped as a circle with a diameter of 2 cm. In this example, the distance between B and A is 1.0 cm., between C and A, 2.0 cm., between D and A, 2.53 cm., between E and A, 7.0 cm., between F and A, 7.47 cm., between G and A, 12.0 cm., and between H and A, 13.0 cm. In addition, dimension I in this example is 0.5 cm. (2 places, J, 2.0 cm., K, 5.0 cm., and L, 5.0 cm.)

These numerical dimensions are intended to define only one embodiment of the subject invention, are intended to be exemplary dimensions only, and are not meant to be limiting. Therefore, other embodiments are intended to be within the scope of the invention.

Finally, the wire retainer/label is placed over the holes in the foam backing after the exposed ends of the wires have been inserted and electrically coupled to the metal foils. The wire retainer is coated with an adhesive so that it will adhere to the foam backing and reduce strain on the wires. Also, the monitoring and stimulating insulated wires are bonded together to prevent their becoming twisted with one another.

The multiple pads are preferably physically spaced from one another. The physical isolation of the pads from one another largely makes it possible for a single set of electrodes to more efficiently perform multiple electrical, physiological functions at or about the same time from a single set of electrodes. The reason for this is that one or more conductive pads are devoted exclusively to monitoring, and there is no need to wait for these pads to depolarize since they will never be used for the stimulating function. Because a single set of electrodes is used, the problems of twisted leads and consistent placement associated with the prior art use of multiple sets of electrodes is eliminated. Compared with the prior art sequential use of a single set of electrodes, defibrillating and monitoring from a single set of electrodes can be performed at or about the same time, and pacing and monitoring from a single set of electrodes is possible for the first time.

The pads are preferably composed of conductive, polymer compounds known as hydrogels which are the result of recent, significant advancements in conductive gel technology. A recent article providing more information about the conductive polymers is R. Kaner and A. MacDiarmid, *Plastics That Conduct Electricity*, Scientific American, Vol. 258, No. 2 (Feb. 1988), which is herein incorporated by reference.

The hydrogels offer several advantages over existing saline-based gels. First, the hydrogels have the consistency of rubber, eliminating the smearing problem associated with prior art gels. In addition, because of their rubber-like consistency, the hydrogels have a longer shelf life than the prior art gels, and they do not leave a residue once they are removed from contact with a patient's skin. Finally, the hydrogels need not be integrated with a sponge in order to achieve their shape.

Second, the hydrogels used for the electrodes can be chosen to be inherently adhesive, so that the pads will adhere to a patient's skin over their entire surface area compared with the ring of adhesive surface provided with prior art electrodes. As a result, the pads will adhere better, eliminating the problem of burning and electrode movement during monitoring associated with prior art electrodes.

Third, the hydrogels have better electrical characteristics than the prior art gels. They are lower ia impedance than the present gels, so that less voltage is required to administer a particular stimulating current pulse. As a result, the voltage generator in the cardiac system to which the electrode is integrated, and the entire cardiac system in general, can be made smaller, more compact, and less costly. Also, the hydrogels, because of their different electrochemistry, will depolarize much faster than prior art gels. In fact, the hydrogels will typically depolarize in one-half the time it takes for a prior art gel to depolarize. The faster depolarization of the hydrogels, their rubber-like consistency, and their elimination of smearing further contribute to the ability to perform multiple electrical, physiological functions from a single set of electrodes.

As is clear from the above descriptions, a multi-pad electrode for performing physiological multiple, electrical functions at or about the same time from a single set of electrodes is described.

A cardiac system for performing multiple, electrical physiological functions at or about the same time is illustrated in FIG. 3. As shown in the Figure, the system preferably comprises stimulating means 101, monitoring means 102, and electrode means 103. In the example of FIG. 3, stimulating means 101 further comprises defibrillator 201, defibrillator paddles 202, defibrillator input plates 203, and external pacemaker/defibrillator pass-through 204. As indicated in the Figure, the defibrillator paddles are advantageously electrically coupled to the defibrillator, the defibrillator input plates are advantageously electrically coupled to the pass-through, which in turn is advantageously electrically coupled to the monitoring means. Finally, the electrode means is advantageously electrically coupled to the pass-through.

In the example of FIG. 3, defibrillator 201 is a conventional defibrillator (typically a LIFEPAK 5 by PhysioControl) which delivers defibrillating energy by means of defibrillator paddles 202. In addition, monitoring means 102 is a conventional ECG monitor. Electrode means 103 are preferably a single set of multi-pad, multi-function electrodes of the subject invention described earlier.

Pass-through 204 is an asynchronous external cardiac pacemaker that provides for the combined use of the most important aspects of emergency cardiac treatment. The device is advantageously approximately $6''\times 2''\times 3''$ and contains the circuitry for an external cardiac pacemaker. Moreover, it is designed to mount on top of industry standard defibrillators to enhance the treatment of heart attack victims, and the device is designed to operate for 2-3 hours on two disposable 9V alkaline batteries. It advantageously has three pacing rates, 60, 80 and 100 beats per minute, and two pacing amplitudes, 100 and 150 milliamperes (mA). Pacing or defibrillating current is delivered through the electrodes. External cardiac pacing is an old and proven technique for initiating a heart contraction.

The defibrillator input plates located on the top of the pass-through are spring loaded and provide the ability to defibrillate and pace through the same set of electrodes. When one plate is depressed, an intermittent tone is sounded. When both plates are fully depressed, the tone becomes constant, indicating that both plates are down and that defibrillation may follow. Defibrillating energy is then generated and delivered by the defrilator through the pass-through and to the patient through the electrodes. The plates are designed to be depressed by the paddles of any defibrillator with no gel required. After the plates have been depressed by means of the defibrillating paddles, the plates will spring back up and reconnect the pacemaker circuitry to the patient. When both plates are not fully depressed, pacing may follow. Pacing energy is then generated and delivered by the pass-through to the electrodes and ultimately the patient.

The pass-through also provides a connection for a two lead ECG monitor through the pass-through straight to the electrodes. The monitor signal will advantageously pass through the pass-through whether or not it is turned on. Also, no manipulation or alteration of the monitor signal is performed inside the pass-through.

Typical usage of the cardiac system will first consist of the use of the electrodes for monitoring which will enable the determination of treatment. This is typically followed by the initiation of external cardiac pacing through the same set of electrodes. As indicated above, the pass-through will generate and deliver external cardiac pacing energy through the electrodes to a patient automatically when both input plates are not fully depressed. Should defibrillation be necessary, the paddles will be firmly pressed against the plates until both are depressed and the resultant tone is constant, and the defibrillator will generate and deliver defibrillating energy through the electrodes to the patient. Additional monitoring can then be performed, and additional treatment in the form of external pacing can be immediate.

Additional advantages and modifications will readily occur to those skilled in the art. The invention in its broader aspects is not, therefore, limited to the specific details, representative methods, and illustrative examples shown and described. Accordingly, departures may be made from such details without departing from the spirit or scope of applicant's general inventive concept.

What is claimed is:

1. A non-invasive electrode comprising:
   at least two spaced conductive polymer pads, each pad having a surface arranged to be placed in contact with a patient, for stimulating and monitoring the patient's heart at or about the same time wherein at least a first one of said conductive polymer pads has an area determined effective for cardiac stimulation, and is adapted for receiving first electrical impulses from stimulating means, and delivering said first electrical impulses to the patient's heart, while at least one other of said conductive polymer pads is adapted for receiving second electrical impulses from that patient's heart and delivering said second impulses to monitoring means at or about the same time said first pad is delivering said first electrical impulses, the other pad being spaced from said first pad by a distance determined effective to substantially isolate the first electrical impulses from the second electrical impulses;
   substantially non-conducting backing means for integrally connecting said first and other pads;
   means for electrically coupling said first pad to said stimulating means; and
   means for electrically coupling said other pad to said monitoring means.

2. The electrode of claim 1 wherein said means for electrically coupling said first pad t said stimulating means comprises means for electrically coupling said first pad to defibrillating means.

3. The electrode of claim 1 wherein said means for electrically coupling said first pad to said stimulating means comprises means for electrically coupling said first pad to pacing means.

4. A non-invasive electrode comprising:
   at least two spaced conductive polymer pads, each pad having a surface arranged to be placed in contact with the patient, for pacing and monitoring the patient's hear at or about the same time, wherein at least a first one of said conductive polymer pads has an area determined effective for cardiac pacing, and is adapted for receiving first electrical impulses from pacing means and delivering said first impulses to the patient's heart, while at leas one other of said conductive polymer pads is adapted for receiving second electrical impulses from that patient's heart and delivering said electrical impulses impulses to monitoring means at or about the same time said first pad is delivering said first electrical impulses, the other pad being spaced from said first pad by a distance determined effective to substantially isolate the first electrical impulses from the second electrical impulses;
   substantially non-conducting backing means for integrally connecting said first and other pads;
   means for electrically coupling said first pad to said pacing means; and
   means for electrically coupling said other pad to said monitoring means.

5. A cardiac system comprising:
   at least a pair of electrodes wherein at least a first one of said electrodes is non-invasive, and has at least two spaced conductive polymer pads integrally connected by means of a substantially non-conducting backing wherein at least a first one of said pads has an area determined effective for cardiac stimulation, and is adapted to receive first electrical impulses from stimulating means and deliver said first electrical impulses to a patient's heart, while at least one other of said pads is adapted to receive second electrical impulses at or about the same time from that patient's heart and to deliver said second electrical impulses to monitoring means;
   stimulating means for producing said first electrical impulses; and
   monitoring means for receiving said second electrical impulses.

6. The system of claim 5 wherein said stimulating means is defibrallating means.

7. A cardiac system comprising:
   at least a pair of electrodes wherein at least a first one of said electrodes is non-invasive, and has at least two spaced conductive polymer pads integrally connected by means of a substantially non-conducting backing wherein at least a first one of said pads has an area determined effective for cardiac pacing, and is adapted to receive first electrical impulses from pacing means and to deliver said first electrical impulses to a patient's heart, while at least one other of said pads is adapted to receive second electrical impulses at or about the same time from that patient's heart and to deliver said second electrical impulses to monitoring means;

pacing means for producing said first electrical impulses; and monitoring means for receiving said second electrical impulses.

8. A cardiac system comprising:

at least a pair of electrodes wherein at least a first one of said electrodes is non-invasive, and has at least two spaced conductive polymer pads integrally connected by means of a substantially non-conducting backing wherein at least a first one of said pads is adapted to receive first electrical impulses and to deliver said first electrical impulses to a patient's heart, while at least one other of said pads is adapted to receive second electrical impulses at or about the same time from that patient's heart and to deliver said second electrical impulses to monitoring means means for generating defibrillating electrical impulses;

means for generating pacing electrical impulses;

coupling means for delivering said first electrical impulses to said first pad, said first electrical impulses comprising a selected one of said defibrillating electrical impulses and said pacing electrical impulses; and monitoring means for receiving said second electrical impulses.

9. A process for stimulating and monitoring a patient's heart at or about the same time utilizing a non-invasive electrode having at least two spaced conductive polymer pads, wherein at least a first one of said pads has an area determined effective for cardiac stimulation, comprising the steps of:

delivering stimulating electrical impulses to said patient's heart through said first pad; and receiving electrical impulses at or about the same time from said patient's heart through at least one other of said pads.

10. The process of claim 9 wherein said delivering step comprises delivering defibrillating electrical impulses.

11. The process of claim 9 wherein said delivering step comprises delivering pacing electrical impulses.

12. The process of claim 9 further comprising the step of displaying a representation of said received electrical impulses.

* * * * *

UNITED STATES PATENT AND TRADEMARK OFFICE
CERTIFICATE OF CORRECTION

PATENT NO. : 5,080,099

DATED : January 14, 1992

INVENTOR(S) : Tim J. Way and L. Allen Butler

It is certified that error appears in the above-identified patent and that said Letters Patent is hereby corrected as shown below:

Col. 5, line 23, replace "13.0" with -- 14.0 --.

Col. 8, line 13, replace "t" with -- to --;
        line 30, replace "leas" with -- least --;
        line 32, after "said" insert -- second --;
        line 33, delete "impulses (first occurrence)"; and
        line 64, replace "defibrallating" with -- defibrillating --.

Signed and Sealed this

Tenth Day of August, 1993

Attest:

MICHAEL K. KIRK

*Attesting Officer*      *Acting Commissioner of Patents and Trademarks*